United States Patent [19]

November

[11] 4,135,383
[45] Jan. 23, 1979

[54] VIBRATION DENSITOMETER PROBE

[75] Inventor: Milton H. November, Hacienda Heights, Calif.

[73] Assignee: International Telephone and Telegraph Corporation, New York, N.Y.

[21] Appl. No.: 866,030

[22] Filed: Dec. 30, 1977

[51] Int. Cl.² .............................................. G01N 9/00
[52] U.S. Cl. ................................................... 73/32 A
[58] Field of Search .................. 73/32 A, 651; 310/25

[56] References Cited

U.S. PATENT DOCUMENTS 3,878,710   4/1975   Miller .................................. 73/32 A Primary Examiner—Jerry W. Myracle
Attorney, Agent, or Firm—A. D. Stolzy

[57] ABSTRACT

A welded vibration densitometer probe to obviate frequency shifts due to temperature changes.

2 Claims, 3 Drawing Figures

VIBRATION DENSITOMETER PROBE

BACKGROUND OF THE INVENTION

This invention relates to vibration densitometers, and more particularly to a temperature insensitive vibration densitometer probe.

PRIOR ART STATEMENT

The probe of the present invention may be employed in one or more of the densitometers disclosed in some of the following United States patents.

The probe of the present invention may be similar to that of U.S. Pat. No. 4,037,461. For the issue date, see the following list.

| Patent Numbers | Issue Dates |
| --- | --- |
| 3,677,067 | July 18, 1972 |
| 3,706,220 | December 19, 1972 |
| 3,738,155 | June 12, 1973 |
| 3,741,000 | June 26, 1973 |
| 3,775,597 | November 27, 1973 |
| 3,776,024 | December 4, 1973 |
| 3,783,259 | January 1, 1974 |
| 3,795,136 | March 5, 1974 |
| 3,805,361 | April 23, 1974 |
| 3,808,875 | May 7, 1974 |
| 3,823,310 | July 9, 1974 |
| 3,832,884 | September 3, 1974 |
| 3,842,655 | October 22, 1974 |
| 3,878,374 | April 15, 1975 |
| 3,952,592 | April 27, 1976 |
| 3,958,446 | May 25, 1976 |
| 4,037,461 | July 26, 1977 |

SUMMARY OF THE INVENTION

In accordance with the present invention, in vibration densitometer apparatus, the combination is provided comprising: a pipeline having a flow path; a vibration densitometer probe having an end; means including a hollow shaft in said pipeline for providing a fluid-tight mount on said pipeline for said probe, said mount holding said probe in a position such that said probe end extends into said flow path, said probe hanging from said hollow shaft, said probe including a ferrule, said ferrule including an annular body having a hole therethrough, said hollow shaft extending at least part way into said hole, and a cup-shaped body having an upper rim extending around said ferrule, said ferrule having a flange extending over said rim, said hollow shaft being welded to said ferrule by a weld material, said ferrule being welded to said rim by a weld material, both of said welds being fluid tight.

BRIEF DESCRIPTION OF THE DRAWINGS

In the accompanying drawings which illustrate exemplary embodiment of the present invention.

DESCRIPTION OF THE PREFERRED EMBODIMENT

Figure 1:
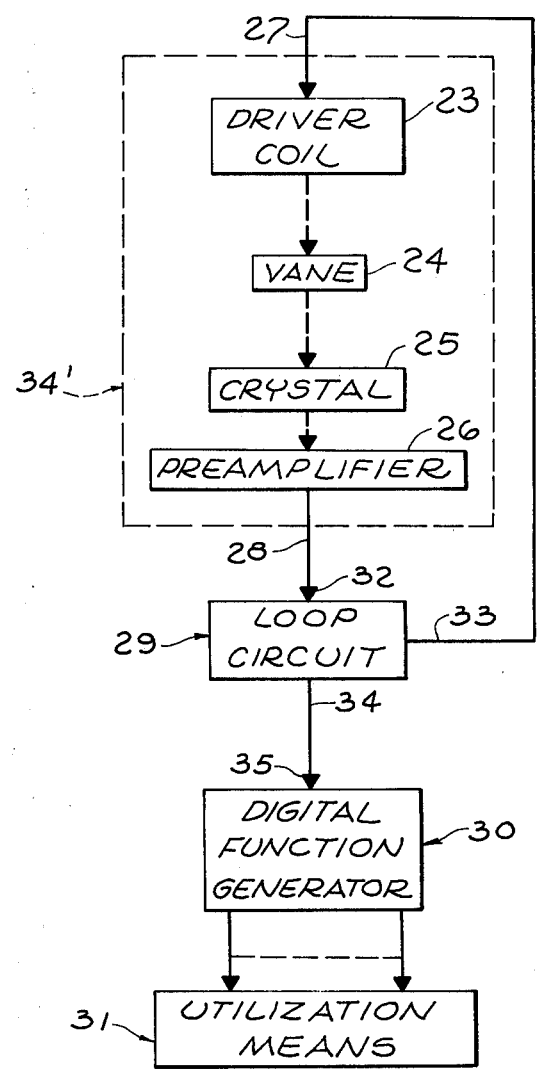
FIG. 1 is a block diagram of a densitometer constructed in accordance with the present invention.

In the drawings, in FIG. 1, a vibration densitometer probe is indicated at 34' having a driver coil 23, a vane 24, a piezoelectric crystal 25 and a preamplifier 26. Probe 34' has an input lead 27 and an output lead 28.

Other blocks shown in FIG. 1 are a loop circuit 29, a digital function generator 30 and utilization means 31. Loop circuit 29 has an input lead 32 and output leads 33 and 34. Digital function generator 30 has an input lead 35 connected from loop circuit output lead 34. The output of digital function generator 30 is connected to utilization means 31.

The output lead 28 of probe 34' is connected to the input lead 32 of loop circuit 29. The input lead 27 of probe 34' is connected from the output lead 33 of loop circuit 29. Probe 34' and loop circuit 29 form a closed loop electromechanical oscillator. Vane 24 is submerged in a fluid. The density of the fluid is a function of the frequency at which vane 24 vibrates.

Digital function generator 30 may have its input lead 35 connected from lead 33 or at other points in loop circuit 29. Loop circuit 20 impresses a square wave voltage on input lead 35 of digital function generator 30 having a mark-to-space ratio of 1:1.

Utilization means 31 shown in FIG. 1 may be a density indicator, a specific gravity indicator, a process controller or otherwise.

Probe 34' shown in FIG. 1 is constructed in accordance with the present invention.

Preamplifier 26 shown in FIG. 1 may be conventional. All of the structures shown in FIG. 1 may be identical to those shown in U.S. Pat. Nos. 3,878,374 and 3,958,446 except probe 34'.

OPERATION

In the embodiment of the invention shown in FIG. 1, probe 34' and loop circuit 29 provide an electromechanical oscillator which oscillates at a frequency dependent upon the density of the fluid in which vane 24 is immersed. The same is true of the pulse repetition frequency of the square wave voltage applied to the input lead 35 of digital function generator 30.

Digital function generator 30 may be described as a digital linearization circuit. It produces a digital output directly proportional to density from the input signal thereto impressed upon the input lead 35 thereto.

Figure 2:
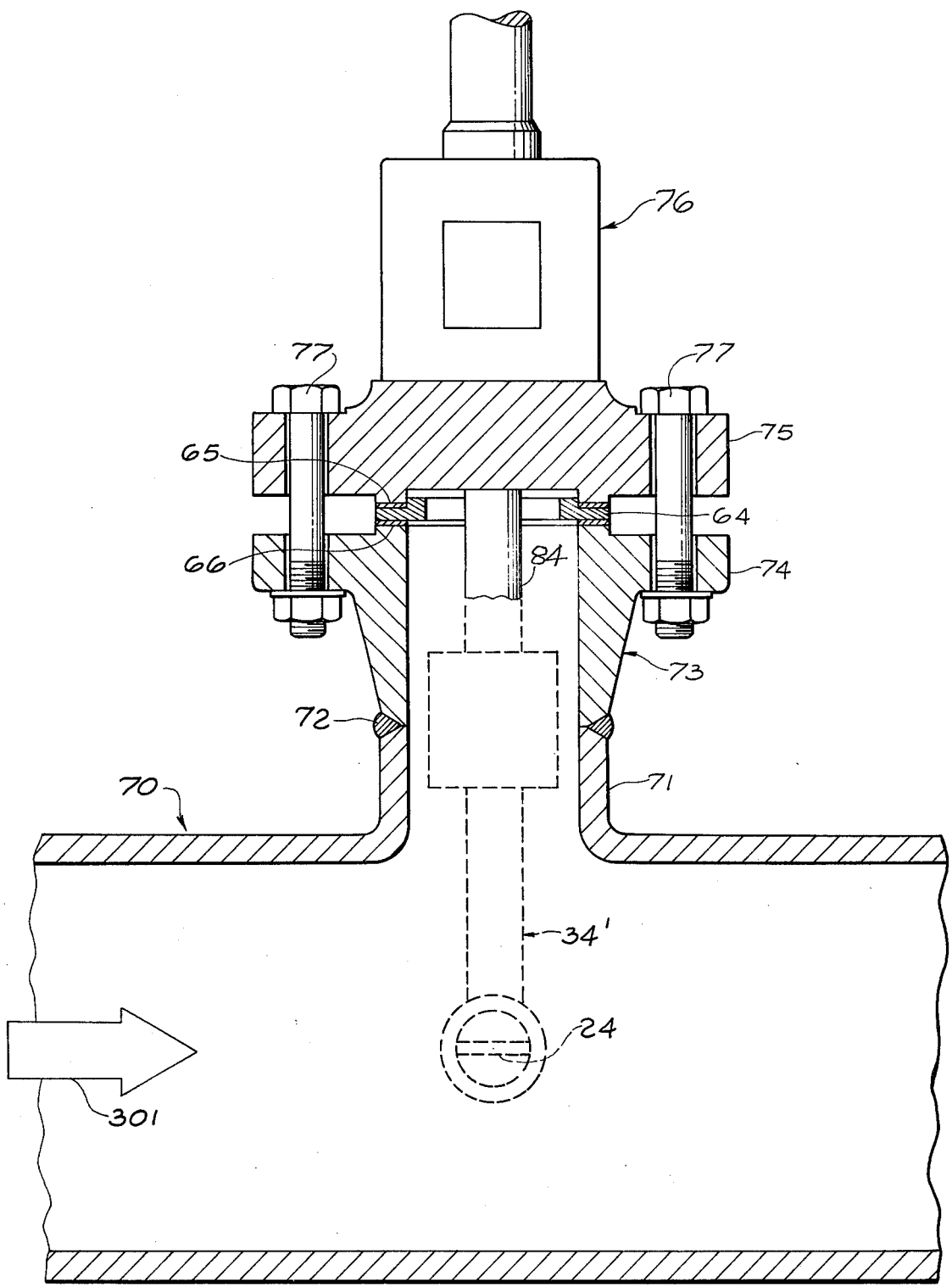
FIG. 2 is a vertical sectional view, partly in elevation, through a pipeline having a portion of the densitometer probe of the present invention mounted therein.

A cylindrical hollow shaft 84 is shown in FIG. 2 including vane 24. Annular gaskets 65 and 66 are provided which are bonded on opposite sides of a ring 64.

Fluid flow may be in the direction of an arrow 301.

A pipeline is illustrated at 70 having a hollow cylindrical projection 71 which is welded at 72 to a fitting 73 that has a flange 74 bolted to a flange 75 of an assembly 76 at preferably three or more or, for example, eight places 77.

Figure 3:
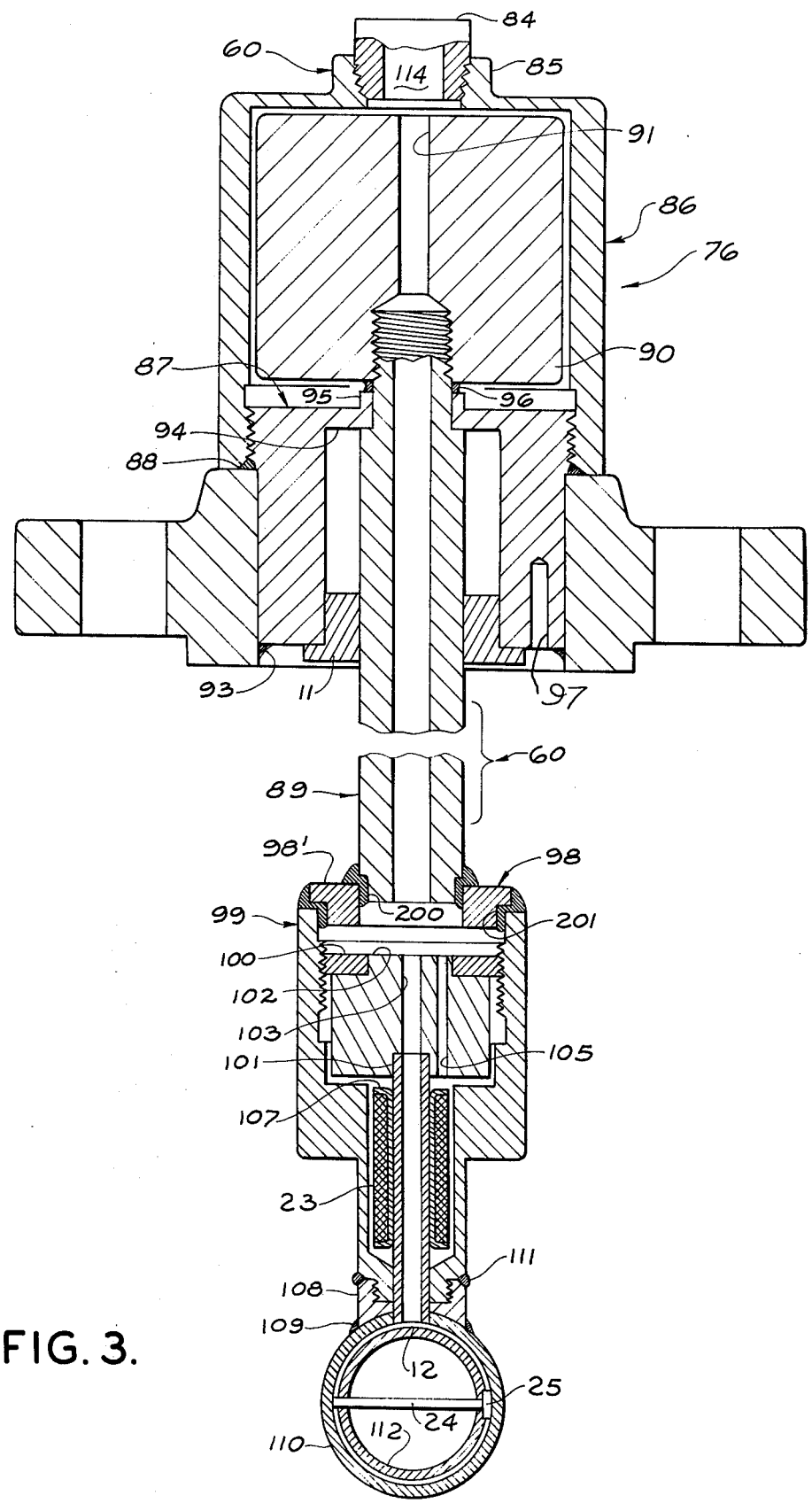
FIG. 3 is a vertical sectional view through a portion of the densitometer probe illustrated in FIG. 2.

A vertical sectional view of probe 34' of FIGS. 1 and 2 is shown in FIG. 3. Ferrule 11 may or may not be employed in a manner identical to that disclosed in U.S. Pat. No. 4,037,461 cited previously. If used, ferrule 11 is fixed to a body 87. Assembly 76 includes shaft 84 of probe 60 threaded into a hollow cylindrical projection 85 of an end cap 86. End cap 86 is threaded to body 87. Flange 75, end cap 86 and body 87 are welded or soldered together at 88. A hollow shaft 89 is externally threaded into a cylinder 90 that is solid except for a hole 91 which extends completely therethrough and is in communication with the hollow interior 92 of shaft 89. Body 87 is welded at 93 to flange 75, and is provided with a thin web 94 which has an upwardly extending cylindrical projection 95 that is welded at 96 to shaft 89 and to cylinder 90. Body 87 may be provided with a pin hole 97, if desired, so that it may be held while end cap 86 is turned or threaded thereto.

Shaft 89 is, in turn, welded at 200 to a ferrule 98 having a flange 98'. Ferrule 98, in turn, is welded at 201 to a cup-shaped body 99.

A ring 100 is threaded into a lower portion of body 99. A magnetostrictive tube 101 which is hollow and open at both ends is press fit into a body 102. Body 102 may have one hole 103 to receive conventional lead wires (not shown) from a piezoelectric crystal 25. See the cited patents. For example see U.S. Pat. No. 3,677,067. Body 102 also may have a hole 105 to receive lead wires from a drive coil 23 wound on a dielectric spool 107 press fit onto tube 101. Again see the said patents. A ferrule 108 is welded at 109 to a cylinder 110. Body 99 is threaded into ferrule 108 and welded thereto at 111. Tube 101 extends, at the bottom thereof, through a circular hole 12 in cylinder 110 and bears against the external cylindrical surface of a cylinder 112. Vane 24 is fixed inside cylinder 110 in any conventional manner. The same is true of crystal 25.

The utility of a vibration densitometer employing the structure disclosed herein is described in detail in the last-mentioned patent.

Cylinders 110 and 112, vane 24, and crystal 25 may be identical to those disclosed in the last-mentioned patent, if desired. Tube 101 is slidable through the lower end of body 99 and is conventionally slidable through the said circular hole 12 through cylinder 110.

A more detailed explanation of the operation of a vibration densitometer employing the structure disclosed herein is set forth in the said last-mentioned patent.

It is common to use a preamplifier in the probe. Such a preamplifier may be employed at 114 in FIG. 3, or at any other convenient location, as desired.

It has been unexpectedly discovered that the welds (rather than threaded connections) at 200 and 201 make the probe 34' temperature insensitive. For example, in use, the frequency of the unit was checked at one atmosphere (Boulder, Colo.). It then was lowered in temperature to −40° F., raised in temperature to 160° F., and returned to room temperature. The terminal frequency corresponded to the frequency at start of test within 0.02 Hz. (loop circuit input) for a single temperature cycle. This was a significant performance improvement over the prior art.

The probe 34' may be identical to the probe shown in the said U.S. Pat. No. 3,741,000 except for the utilization of the said welds inside and outside of ferrule 98 for threaded connections.

It is an outstanding feature of the present invention that, for example, the temperature of the densitometer was lowered to −40° F., raised to 100° F., and returned to room temperature where it had been originally. In this case, the frequency, after the temperature cycle, had changed only 0.02 Hz.

What is claimed is:

1. In vibration densitometer apparatus, the combination comprising: a pipeline having a flow path; a vibration densitometer probe having an end; means including a hollow shaft in said pipeline for providing a fluid tight mount on said pipeline for said probe, said mount holding said probe in a position such that said probe end extends into said flow path, said probe hanging from said hollow shaft, said probe including a ferrule, said ferrule including an annular body having a hole therethrough, said hollow shaft extending at least part way into said hole, and a cup-shaped body having an upper rim extending around said ferrule, said ferrule having a flange extending over said rim, said hollow shaft being welded to said ferrule by a weld material, said ferrule being welded to said rim by a weld material, both of said welds being fluid tight.

2. The invention as defined in claim 1, wherein said hollow shaft and said ferrule are spaced apart a distance and defining an annular space therebetween, said distance being sufficiently large so as to allow the said weld material thereof to occupy the said annular space, said ferrule and said rim being similarly spaced apart a distance and defining an annular space therebetween, said last-named distance being sufficiently large so as to allow the said weld material thereof to occupy the said annular space.

* * * * *